US006410565B1

(12) United States Patent
Cullinan

(10) Patent No.: US 6,410,565 B1
(45) Date of Patent: Jun. 25, 2002

(54) α1-ADRENERGIC RECEPTOR ANTAGONISTS

(75) Inventor: George Joseph Cullinan, Trafalgar, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/869,406

(22) PCT Filed: Jan. 21, 2000

(86) PCT No.: PCT/US00/01449
§ 371 (c)(1),
(2), (4) Date: Jun. 22, 2001

(87) PCT Pub. No.: WO00/45806
PCT Pub. Date: Aug. 10, 2000

Related U.S. Application Data
(60) Provisional application No. 60/118,369, filed on Feb. 3, 1999.

(51) Int. Cl.[7] ..................... A61K 31/445; A61K 31/135
(52) U.S. Cl. ................ 514/320; 514/324; 514/648
(58) Field of Search ................ 514/320, 324; 514/648

(56) References Cited

U.S. PATENT DOCUMENTS

| | | | |
|---|---|---|---|
| 4,418,068 A | | 11/1983 | Jones |
| 5,470,883 A | * | 11/1995 | Stromberg .............. 514/648 |
| 5,484,798 A | | 1/1996 | Bryant et al. |
| 5,567,714 A | | 10/1996 | Bruns, Jr. et al. |
| 5,846,976 A | | 12/1998 | Batchelor et al. |

FOREIGN PATENT DOCUMENTS

| | | |
|---|---|---|
| DE | 33 23 321 | 1/1985 |
| EP | 0 659 426 | 12/1994 |
| EP | 0 668 075 | 12/1994 |
| WO | WO 96/40135 | 6/1995 |
| WO | WO 96/09040 | 3/1996 |
| WO | WO 97/44029 | 5/1996 |
| WO | WO 97/44029 | * 11/1997 |

OTHER PUBLICATIONS

Franco L.G., et al., "Tomixifen a new proposed treatment for scleroderma and Raynaud's disease preliminary study using fingertip temperature measurements" Database Biosis "Online", *Biosciences Information Service and Revista Argentina De Dermatologica* 69(3) pp. 168–176 (1988).

Grese, Timothy A., et al., "Molecular determinants of tissue selectivity in estrogen receptor modulators" *National Academy of Sciences* 94 pp. 14105–14110 (1997).

Hoffman, Brian B., et al. "Adrenergic Receptor Antagonists" *The Pharmacological Basis of Therapeutics*, Eighth Edition, pp 221–229 (1990).

Kenny, Barry et al., "Pharmacological Options in the Treatment of Benign Prostatic Hyperplasia" *Journal of Medicinal Chemistry* 40(9) pp. 1293–1315 (1997).

Palkowitz, Alan D. "Discovery and Synthesis of [6-Hydroxy-3-[4-[2-(1-piperidinyl)ethoxy]phenoxyl-2-(4-hydroxyphenyl)]benzo [b]thiophene: A Novel, Highly Potent, Selective Estrogen Receptor Modulator" *Journal of Medicinal Chemistry* 40(10) pp. 1407–1416 (1997).

* cited by examiner

*Primary Examiner*—Raymond Henley, III
(74) *Attorney, Agent, or Firm*—Gilbert T. Voy

(57) ABSTRACT

The present invention relates to an α1-adrenergic receptor antagonist of formula I

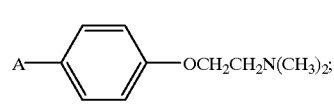

or an N-oxide or pharmaceutical salt or solvate thereof; wherein A is a moiety selected from the group consisting of:

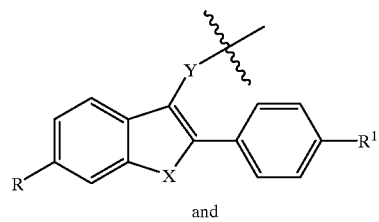

and

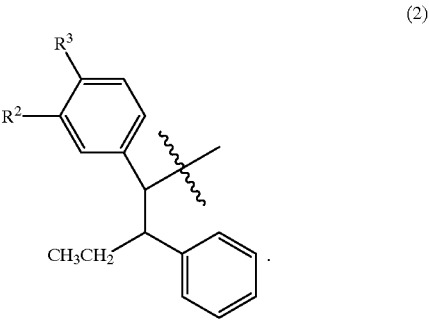

10 Claims, No Drawings

α1-ADRENERGIC RECEPTOR ANTAGONISTS

This application claims is a 371 of PCT/US00/01449 filed Jan. 21, 2000 which priority to U.S. Provisional Application Serial No. 60/118,369, filed Feb. 3, 1999.

FIELD OF THE INVENTION

The current invention pertains to the fields of medicinal chemistry, pharmacology, and medicine. Further, the current invention identifies compounds which are antagonists of the $\alpha_1$-adrenergic receptor.

BACKGROUND OF THE INVENTION

The sympathetic nervous system is a critical system in mammals, including humans. It's major activity is to regulate and maintain homeostasis of a wide variety of functions throughout the body. For example, the sympathetic nervous system provides control and coordinated regulation of several major cell types, among these; smooth muscle, liver, skeletal muscle, nerve, and adipoetic cells.

As a result of the system's effect on smooth muscle cells (constriction or dilation), the sympathetic nervous system is critical in the control (flow and pressure) of fluids in the body, such as air, blood, urine, food, waste, and the like. Similarly, system effects on hepaticytes and adipocytes have a major regulatory function on energy production and utilization. For further details on the function and effects of the sympathetic nervous system, see: "Goodman and Gilman's The Pharmacological Basis of Therapy", Eds. Gilman, A. E., Rall, T. W., Nies, A. S., and Taylor, P., 8th Ed., Pergamon Press, New York, 1990, Ch. 5, pp. 84–95.

On a molecular level, the sympathetic nervous system is primarily activated by the catecholamine neurotransmitters (primarily epinephrine and norepinephrine, and to a much lesser extent, outside the central nervous system, dopamine). For further information see: ibid., Chap. 10 and references cited therein. The action or response of a particular cell type to catecholamine stimuli is dependent on the type of receptor on that cell. Germane to the current invention, are the receptors of the sympathetic nervous system known as adrenergic receptors. Most germane to the current invention are the actions of the α receptor and more specifically the $\alpha_1$ receptor.

The $\alpha_1$ receptor is a major regulatory element on smooth muscle cells. Thus, tissues containing large numbers of these cells are often highly effected by agonist or antagonists to this receptor. Such tissues would include the arterioles, veins, sphincter, trigone, skin, male ejaculatory system, and the like. In general, activation of the $\alpha_1$ receptor causes the smooth muscle cells to contract. Thus, activation may have the effect of constricting the vasculature and raising blood pressure, constricting the urinary tract and restricting urine flow, and the like. Compounds which block the $\alpha_1$ receptor have the opposing effects, i.e., vasodilatation, etc.

Thus, $\alpha_1$ receptor antagonists are potential therapeutic agents for hypertension, congestive heart failure, and other cardiovascular diseases. Additionally, $\alpha_1$ antagonists have been used successfully in increasing urinary flow in patients suffering from benign prostatic hyperplasia (BPH), see: "Pharmacological Options in the Treatment of Benign Prostatic Hyperplasia", Kenny, B., et al., J. Med. Chem., 40(9), pp. 1293–1315 (1997).

Currently, the most widely used compounds which block the $\alpha_1$ receptor are a series of piperazinyl quinazolines, e.g., prazosin, terazosin, doxazosin, and trimazosin. Of these, the most commonly used compound is prazosin (Minipress™). Although, this compound is quite beneficial in lowering blood pressure, it can also cause postural hypotension and syncopal episodes. (For further information, see: "Physician's Desk Reference", 47th Ed., Medical Economics Co., Montvale N.J., 1993, pp. 1834–5). Thus, a need currently exists for new $\alpha_1$ antagonists.

SUMMARY OF THE INVENTION

The current invention relates to a method for antagonizing $\alpha_1$-adrenergic receptors which includes administering, to a mammal in need thereof, an effective amount of a compound of formula I:

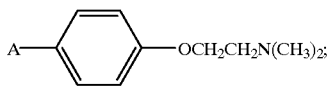

I or an N-oxide or pharmaceutical salt or solvate thereof; wherein A is a moiety selected from the group consisting of:

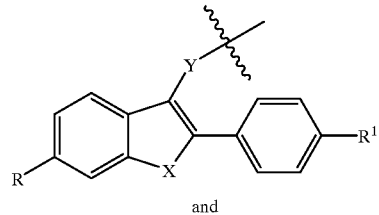

(1)

and

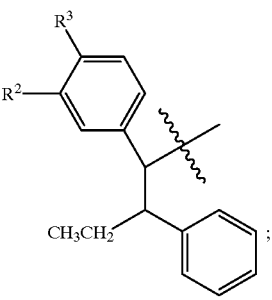

(2)

wherein:
R and $R^1$ are independently hydrogen, hydroxy, chloro, bromo, $C_1$–$C_4$ alkyl, $C_1$–$C_4$ alkoxy, $OCOC_1$–$C_6$ alkyl, OCO(phenyl), or OCO(substituted phenyl);
X is oxygen or sulfur; and
Y is oxygen, $CH_2$, or CO.

The present invention further relates to a method of inhibiting the pathological states or sequelae resulting from inappropriate activation of $\alpha_1$-adrenergic receptors comprising administering, to a mammal in need thereof, an effective amount of a compound of formula I.

Moreover, the present invention relates to the use of a compound of formula I for the manufacture of a medicament useful as an antagonist of the $\alpha_1$-adrenergic receptor.

In addition, the present invention relates to the use of a compound of formula I for the manufacture of a medicament for the inhibition of pathological states or sequelae resulting from inappropriate activation of the $\alpha_1$-adrenergic receptor.

DETAILED DESCRIPTION OF THE INVENTION

General terms used in the description of compounds herein described bear their usual meanings. For example, "$C_1$–$C_6$ alkyl" refers to straight or branched aliphatic chains of 1 to 6 carbon atoms including methyl, ethyl, propyl, iso-propyl, n-butyl, pentyl, hexyl and the like. $C_1$–$C_6$ alkyl includes those moieties referred to as "$C_1$–$C_4$ alkyl". The term "$C_1$–$C_4$ alkoxy" refers to a $C_1$–$C_4$ alkyl group attached through an oxygen bridge and includes such groups as methoxy, ethoxy, n-propoxy, iso-propoxy, and the like.

The term "substituted phenyl" refers to a phenyl group having one to five substituents selected from the group consisting of: $C_1$–$C_4$ alkyl, $C_1$–$C_4$ alkoxy,, hydroxy, nitro, chloro, fluoro, or tri(chloro or fluoro)methyl.

A "N-oxide" of a compound of formula I has the following structure:

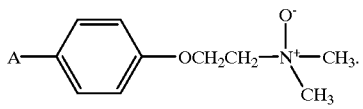

In general, the term "pharmaceutical" when used as an adjective means substantially non-toxic to mammals. For example, the term "pharmaceutical salt" as used herein, refers to salts of the compounds of formula I which are substantially non-toxic to mammals. See, e.g., Berge, S. M, Bighley, L. D., and Monkhouse, D. C., "Pharmaceutical Salts", *J. Pharm. Sci.*, 66:1, 1977. These pharmaceutical salts frequently have enhanced solubility characteristics compared to the compound from which they are derived and, thus, are often more amenable to formulation as liquids or emulsions.

The term "solvate" represents an aggregate that comprises one or more molecules of the solute, such as a formula I compound, with one or more molecules of a pharmaceutical solvent. Such solvent molecules would be those commonly used in the pharmaceutical arts, which are known to be innocuous to the recipient, e.g., water, ethanol, and the like.

As used herein, the term "effective amount of a compound of formula I" refers to an amount of a compound of the present invention which is capable of antagonizing $\alpha_1$-adrenergic receptors and/or inhibiting the pathological states or sequelae resulting from inappropriate activation of $\alpha_1$-adrenergic receptors.

The term "inhibit" and "inhibiting" refer to preventing, prohibiting, halting, restraining, slowing or reversing the progression of pathological states or sequelae resulting from inappropriate activation of $\alpha_1$-adenergic receptors.

"Pathological states or sequelae resulting from inappropriate activation of $\alpha_1$-adrenergic receptors" include, but are not limited to: primary systemic hypertension, congestive heart failure, coronary vasospasm, digital vasospasm due to Raynaud's syndrome, ventricular arrhythmias, urinary resistance due to trauma or benign prostatic hypertrophy, premature ejaculation, dilation of the iris, increased secretion of the bronchial glands, decreased sweating, and the like. The methods of the current invention contemplate not only treatment of these conditions, but prevention in appropriate circumstances.

A preferred embodiment of the current invention is the administration of a compound of formula I where A is a moiety of the formula (1) and X is sulfur. Even more preferred is the administration of the hydrochloride salt of a compound of formula I where R and $R^1$ are hydroxy.

Another preferred embodiment of the current invention is the administration of the citrate salt of a compound of formula I wherein A is a moiety of the formula (2).

The compounds of formula I wherein A is a moiety of the formula (1) and X is sulfur, can be prepared by the methods described in U.S. Pat. Nos. 4,133,814, 4,418,068, 5,393,763, 5,484,798, 5,492,926, and 5,510,357, also, Jones, C. D., et al., *J. Med. Chem.*, 27(8), pp. 1057–1066 (1984) and Palkowitz, A. D., et al., *J. Med. Chem.*, 40(10), pp. 1407–1416 (1997), the teachings of which are incorporated by reference.

Compounds of the current invention where A is a moiety of the formula (1) and X is oxygen can be prepared by known variations of the references cited, supra, or by the methods described in the PCT application WO 96/09040, the teachings of which are incorporated by reference herein.

Compounds where A is a moiety of the formula (2) may be prepared as taught in U.S. Pat. No. 4,536,516, the teachings of which are incorporated by reference. The citrate salt of such a compound is the known, commercial compound, tamoxifen citrate (NOLVADEX™, Zeneca Pharmaceuticals, Wilmington, Del., 19897).

Assays measuring the antagonist properties of the compounds of the invention were performed by methods similar to those described by Greengrass, P. and Bremner, R., "Binding Characteristics of $^3$H-Prazosin to Rat Brain Alpha-adrenergic Receptors", *Eur. J. Pharmacol*, 55, pp. 323–326 (1979). Frozen, whole rat brain tissue was homogenized using a Brinkman Polytron PT-10. The tissue was homogenized in 25 volumes of 0.25M sucrose and centrifuged at 1000×g for 10 minutes. The supernatant was centrifuged at 40,000×g for an additional 10 minutes. The resulting pellet was resuspended in Tris, 50 mM, pH 7.7 buffer and again centrifuged at 40,000×g for 10 minutes. The resulting pellet was resuspended in the buffer. The radiolabel ligand, $^3$H prazosin, (New England Nuclear, Boston Mass.) at 0.2 nM was added along with increasing amount of the test compounds and membrane aliquots at a final volume of 1 mL. The test aliquots were incubated at 23° C. for one hour. Assays were terminated by filtration over Whatman GF/B glass-fiber filters on a Brandel cell harvester, followed by an ice-cold wash with 10 mL of saline. Filters were presoaked in 0.1% polyethylimine. Radioactivity bound was determined after a period of equilibrium (at least five hours) in a Fischer ScintiSafe Econo 1 Scintillation Cocktail using a Beckman LS5000 TA counter with an efficiency of approximately 43%. Affinity constants ($K_i$) were determined using nonlinear least squares regression software, Graphad Inplot Inc., San Diego Calif. Affinity $K_i$ were determined from an eleven-point concentration curve and are the mean +/– SE of at least three experiments. The following representative compounds of the current invention were tested in the above assay and exhibited antagonist activity.

[2-(4-hydroxyphenyl)-6-hydroxybenzo[b]thien-3-yl][4-[2-(N,N-dimethylamino)ethoxy]phenyl]methanone hydrochloride;

2-(4-hydroxyphenyl)-3-(4-[2-(N,N-dimethylamino)ethoxy] phenoxy)-6-hydroxybenzo[b]thiophene hydrochloride;

[2-(4-hydroxyphenyl)-6-hydroxybenzo[b]thien-3-yl][4-[2-(N,N-dimethylamino)ethoxy]phenyl]methane hydrochloride; and tamoxifen citrate.

Pharmaceutical formulations of the present invention can be prepared by procedures known in the art using well-known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

The following formulation examples are illustrative only and are not intended to limit the scope of the present invention in any way.

Formulation 1
Gelatin Capsules
Hard gelatin capsules are prepared using the following:

| Ingredient | Quantity (mg/capsule) |
| --- | --- |
| Compound of formula I | 0.001–200 |
| Starch, NF | 0–650 |
| Starch flowable powder | 0–650 |
| Silicone fluid 350 centistokes | 0–15 |

The formulation above may be changed in compliance with the reasonable variations provided.

Formulation 2
Tablets
A tablet formulation is prepared using the ingredients below:

| Ingredient | Quantity (mg/tablet) |
| --- | --- |
| Compound of formula I | 0.001–200 |
| Cellulose, microcrystalline | 200–650 |
| Silicon dioxide, fumed | 10–650 |
| Stearate acid | 5–15 |

The components are blended and compressed to form tablets.

Formulation 3
Tablets
Tablets each containing 2.5–1000 mg of active ingredient are made up as follows:

| Ingredient | Quantity (mg/tablet) |
| --- | --- |
| Compound of formula I | 0.001–200 |
| Starch | 45 |
| Cellulose, microcrystalline | 35 |
| Polyvinylpyrrolidone | 4 |

-continued
Formulation 3
Tablets
Tablets each containing 2.5–1000 mg of active ingredient are made up as follows:

| Ingredient | Quantity (mg/tablet) |
| --- | --- |
| (as 10% solution in water) Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Formulation 4
Suspensions
Suspensions each containing 0.1–1000 mg of medicament per 5 ml dose are made as follows:

| Ingredient | Quantity (mg/5 ml) |
| --- | --- |
| Compound of formula I | 0.001–200 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Particular clinical protocols for the use of the current invention would depend on the condition being treated, its severity, and extenuating circumstances. Such decisions are best left to the attending physician; however, in general, doses for the contemplated methods of the current invention would be between 10 and 200 mg per day either by a single or split administration via the oral route. Preferably, the dose range would be 10 to 100 mg per day in a split dose regiment.

I claim:

1. A method for antagonizing the $\alpha_1$-adrenergic receptor comprising administering, to a mammal in need thereof, an effective amount of a compound of formula I:

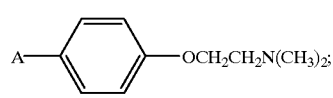

I or an N-oxide or pharmaceutical salt or solvate thereof; wherein A is a moiety selected from the group consisting of:

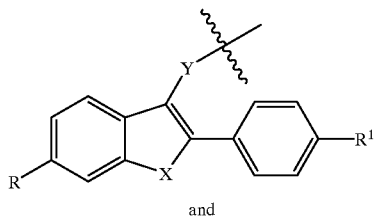

(1)

and

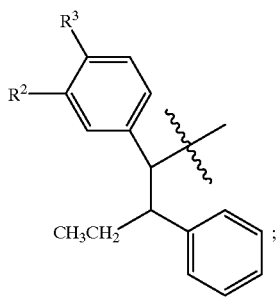

(2)

wherein:

R and $R^1$ are independently hydrogen, hydroxy, chloro, bromo, $C_1$–$C_4$ alkyl, $C_1$–$C_4$ alkoxy, $OCOC_1$–$C_6$ alkyl, OCO(phenyl), or OCO(substituted phenyl);

X is oxygen or sulfur; and

Y is oxygen, $CH_2$, or CO.

2. The method according to claim 1 wherein the mammal is a human.

3. The method according to claim 2 wherein A is a moiety of the formula (1) and X is sulfur.

4. The method according to claim 3 wherein the compound administered is the hydrochloride salt and R and $R^1$ are hydroxy.

5. The method according to claim 2 wherein the compound administered is the citrate salt and A is a moiety of the formula (2).

6. A method of inhibiting the pathological states or sequelae resulting from inappropriate activation of the $\alpha_1$-adrenergic receptor wherein said pathological state or sequelae is selected from the group consisting of: congestive heart failure and urinary constriction; comprising administering, to a mammal in need thereof, an effective amount of a compound of formula I:

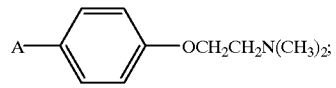

I or an N-oxide or pharmaceutical salt or solvate thereof; wherein A is a moiety selected from the group consisting of:

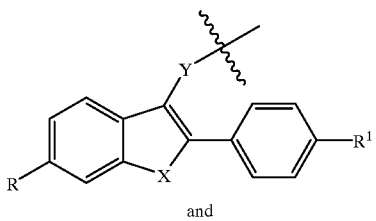

(1)

and

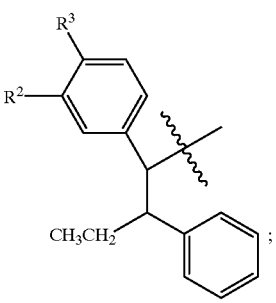

(2)

wherein:

R and $R^1$ are independently hydrogen, hydroxy, chloro, bromo, $C_1$–$C_4$ alkyl, $C_1$–$C_4$ alkoxy, $OCOC_1$–$C_6$ alkyl, OCO(phenyl), or OCO(substituted phenyl);

X is oxygen or sulfur; and

Y is oxygen, $CH_2$, or CO.

7. The method according to claim 6 wherein the mammal is a human.

8. The method according to claim 7 wherein A is a moiety of the formula (1) and X is sulfur.

9. The method according to claim 8 wherein the compound administered is the hydrochloride salt and R and $R^1$ are hydroxy.

10. The method according to claim 7 wherein the compound administered is the citrate salt and A is a moiety of the formula (2).

* * * * *